United States Patent [19]

Schneider

[11] 4,028,153

[45] June 7, 1977

[54] EXPLOSIVE COMPOSITION CONTAINING ALKYL ETHERS HAVING HIGH DENSITIES

[75] Inventor: Abraham Schneider, Overbrook Hills, Pa.

[73] Assignee: Suntech, Inc., St. Davids, Pa.

[22] Filed: Mar. 29, 1976

[21] Appl. No.: 671,635

[52] U.S. Cl. .................................. 149/46; 149/45; 149/61; 102/23

[51] Int. Cl.² ........................................ C06B 31/28

[58] Field of Search ............ 149/61, 46, 45; 102/23

[56] References Cited

UNITED STATES PATENTS 3,240,641  3/1966  Wilson ................................ 149/46

Primary Examiner—Stephen J. Lechert, Jr.
Attorney, Agent, or Firm—Donald R. Johnson; J. Edward Hess; Anthony Potts, Jr.

[57] ABSTRACT

A blasting composition comprising a mixture of inorganic nitrate and a sensitizer containing at least 30 weight percent of an alkyl ether of Binor-S has substantially more explosive force than an equal volumetric amount of a mixture of ammonium nitrate and diesel fuel. The latter is used in large quantities as a commercial explosive. The sensitizer containing the ether is a liquid having a low pour point, high density and high net volumetric heat of combustion compared to diesel fuel.

5 Claims, No Drawings

EXPLOSIVE COMPOSITION CONTAINING ALKYL ETHERS HAVING HIGH DENSITIES

BACKGROUND OF THE INVENTION

This invention is directed to a new and useful improvement to an explosive. In particular it is directed to an improved explosive useful as a blasting composition. More particularly it is directed to a blasting composition containing a nitrate and a nonexplosive sensitizer. Even more particularly it is directed to a nonexplosive sensitizer which is in part carbonaceous. And the improvement resides in the selection of the carbonaceous sensitizer and in particular a hydrocarbon containing oxygen sensitizer. A sensitizer increases the tendency of an explosive material towards detonation. The invention is also directed to an improved method of blasting using the aforementioned blasting composition.

DESCRIPTION OF THE PRIOR ART

Use of a mixture of inorganic nitrates in an explosive is known, see U.S. Pat. No. 3,367,805. Use of a mixture of inorganic nitrates, including ammonium nitrate, and a combustible organic material is known see Kirk-Othmer, ENCYCLOPEDIA OF CHEMICAL TECHNOLOGY, 2nd Edition, Vol. 8, section titled "Explosives." Use of a mixture of ammonium nitrate and a certain hydrocarbon, such as diesel fuel, as an explosive is known, see U.S. Pat. No. 3,061,488, or THE SCIENCE OF HIGH EXPLOSIVES, M. A. Cook, publisher American Chemical Society, 1958, ACS Monograph Series No. 139 or *Iron Ore Co. of Canada v. Dow Chemical Co.*, 177 USPQ 33.

A mixture of prilled ammonium nitrate (about 94%) and diesel fuel (about 6%) is a commercially explosive used in large quantities in blasting. The foregoing mixture will be termed AN-DF hereinafter. Blasting refers to industrial and engineering operations wherein mechanical work is performed such as quarrying, ore dislodgement, ditching, excavating, etc., with a low expenditure of time and money. Blasting is used in open pit mining of coal, iron ore, shale oil,, tar sands, salt and the like. Details of blasting are discussed in ENCYCLOPEDIA BRITANNICA, Vol. 3, Library of Congress Catalog Card No. 69-10039.

An AN-DF mixture can be considered an oxygen-balanced mixture for the following reason. When only ammonium nitrate is decomposed the products generally are nitrogen, water and oxygen. Thus by itself ammonium nitrate contains an excess of oxygen. However, if diesel fuel is added to the ammonium nitrate in a sufficient amount so that there is enough carbon and hydrogen to stoichiometrically react with the excess oxygen, the mixture is said to be balanced as to the available oxygen. As a result the formation of the additional gases, that is, $CO_2$ and $H_2O$ by the reaction of the carbon and hydrogen of the diesel fuel with the excess oxygen from ammonium nitrate substantially increases the explosive force of AN-DF mixture compared to just ammonium nitrate.

An AN-DF mixture is often used in the following manner. A hole is drilled into the rock, for example. A suitable amount of the loose, unpackaged AN is poured into the hole followed by a sufficient amount of DF. The resulting mixture is confined and detonated by a suitable blasting cap. Confinement refers to the practice of filling the remainder of the hole with drilled material or other substances such as rock. Confinement increases the efficiency of the explosion.

However, when blasting in a cold environment a problem can occur. The problem occurs because a typical diesel fuel's pour point is about $-10°$ to $-20°$ F. Pour point is a temperature at which an oil ceases to flow. Thus the use of AN-DF mixture can be restricted by the ambient temperature. Furthermore, at a lower temperature, but above a pour point, the diesel fuel's viscosity may be so high so that when it is poured into a drilled hole containing ammonium nitrate it does not properly fill the hole. Also under such conditions the diesel fuel may not flow into the voids between the ammonium nitrate particles. For either one or both reasons, when the AN-DF mixture is detonated, the maximum possible force is not obtained thereby increasing costs.

SUMMARY OF THE INVENTION

The foregoing low temperature problem is avoided by use of applicants' improved blasting composition. The latter contains an inorganic nitrate, such as ammonium nitrate, or a mixture of nitrates and a liquid sensitizer containing an alkyl ether of Binor-S.

A sensitizer containing an alkyl ether of Binor S has an advantage of having, relative to diesel fuel, a low pour point, a high density and a high net volumetric heat of combustion. For example, as discussed hereinafter, a sensitizer containing about 40% of alkyl ether of Binor-S has a pour point of $-75°$ F, a density of 1.0987 and a net volumetric heat of combustion of 159,600 BTU per gallon. By comparison, a diesel fuel has a pour point of as low as about $-10°$ to $-20°$ F, a density of 0.87 and a net heating value of combustion of about 127,000 BTU per gallon.

Furthermore, because the foregoing ethers contain oxygen, the presence of the oxygen facilitates the complete conversion of the carbon and hydrogen to carbon dioxide and water. Such conversion increases the blasting effect from a given amount of the mixture.

In addition, because the foregoing ethers have such higher heating values more blasting force can be obtained from the material contained in a given size hole. Also because they have such higher densities, more nitrate can be placed in a given size hole which results in more blasting force per hole. Thus less holes need to be drilled. Another advantage is that a smaller hole can be used without reducing the blasting force. It should be realized that the number of holes drilled or the size of the hole drilled can be economically important since drilling amounts to an appreciable part of the cost in blasting. Another advantage results because the foregoing hydrocarbons are so much denser than the fuel oil. The increased density means that much less material has to be transported. For operations within the Arctic Circle, for example, transportation cost far exceeds the initial purchase price of the material. Thus a large saving results from reducing transportation costs.

Another advantage of present invention results from the fact that the sensitizer containing the ether is less viscous than diesel fuel at very low temperatures. Because of the lower viscosity, a more finely ground ammonium nitrate i.e., a higher bulk density ammonium nitrate, could be used. And even with the higher bulk density nitrate the use of the aforementioned sensitizer results in the uniform wetting of the nitrate thereby, resulting in a more efficient explosion. The use of a higher bulk density nitrate permits more nitrate to be placed on a given size hole and thus less holes have to be drilled.

DESCRIPTION OF THE INVENTION

The inorganic nitrate used in this invention includes ammonium nitrate ($NH_4NO_3$) and sodium nitrate ($NaNO_3$), which are preferred, and other nitrates such as potassium, calcium and magnesium. Thus the inorganic nitate is selected from the group consisting of ammonium nitrate, mixture of a major amount of ammonium nitrate and a minor amount of sodium nitrate, potassium nitrate, calcium nitrate and magnesium nitrate. The minor nitrate can be just one particular nitrate or a mixture of two or more nitrates. The nitrate should be of sufficient quality to permit its use as an explosive. For example, according to Kirk-Othmer, supra, ammonium nitrate used in the manufacture of military explosive is required to be at least 99.0% pure, and contain no more than 0.02% free nitric acid, 0.05% sulfate, 0.18 water-insoluble material, and 0.05% chloride; it also should be free of alkalinity and nitrites. It is also reported that the commercial grade used in the manufacture of blasting explosive should be of comparable purity. Either the crystalline aggregate or prills (spherical pellets) form of the ammonium nitrate can be used. The ammonium nitrate should be free of large amounts of any additive, such as mineral filler, which would adversely effect the performance or efficiency of the explosive. However, smaller amounts of such additives may be tolerated. Filler is often used to prevent the ammonium nitrate from caking.

Sodium nitrate can be mixed with the ammonium nitrate. The sodium nitrate increases the available oxygen content. The sodium nitrate can be natural material from Chile known as Chilean nitrate or the synthetic material produced, for example, via the neutralization of synthesized nitrogen oxides. Either works substantially equally well. Sodium nitrate is available in crystalline or prill form. However, the sodium nitrate should be free of large amounts of any additive which would seriously adversely effect the performance or efficiency of the explosive. Smaller amounts of such additives could be tolerated.

Analogous standards, as to the aforementioned, apply to the other inorganic nitrates if they are mixed with the ammonium nitrate or sodium nitrate.

When a mixture of ammonium nitrate and other inorganic nitrates are used the ammonium nitrate will comprise generally a major amount and the other nitrates a minor amount. Usually the ammonium nitrate will comprise 65% by weight or more of the total inorganic nitrate content and preferably 75% by weight or more.

The alkyl ether of Binor-S can be represented by the following structures

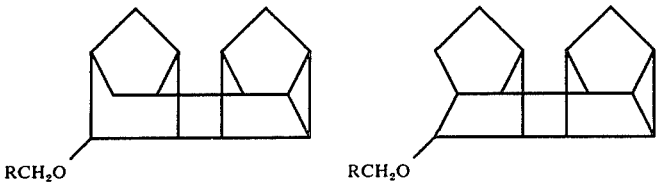

RCH₂O      RCH₂O

The R can be a hydrogen or alkyl containing 1–10 carbon atoms.

Alkyl ethers of Binor-S can be prepared by ionic alcoholysis of Binor-S. The alcoholysis involves contacting the Binor-S with a primary alcohol, hydrogen, hydrogen halide and a catalyst selected from the group consisting of Raney nickel, palladium-on-carbon or palladium-on-alumina. Temperature of the alcoholysis is about 50°–300° C and the pressure is about 100–10,000 psig. Products resulting from the alcoholysis, in addition to any unreacted Binor-S, include hexacyclic alkyl ethers of Binor-S, hexacyclic hydrocarbons and others.

Preparation of Binor-S is disclosed in Journal of The American Chemical Society; 88:21, Nov. 5, 1966, pages 8490–8494, title of article "π" Complex Multicenter Reactions Promoted by Binuclear Catalyst Systems. "Binor-S," a New Heptaheptadiene, by G. N. Schrauzer, B. N. Bastian and G. A. Fosselius. Binor-S is known by its chemical name of endo, cis, endoheptacyclo[5.3.1.1$^{2,6}$.1$^{4,12}$.1$^{9,11}$.0$^{3,6}$.0$^{8,10}$]tetradecane. Its melting point is about 65° C. Binor-S can be depicted by the following structural formula:

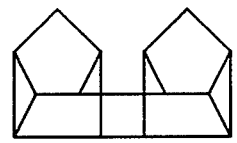

Binor-S is a $C_{14}H_{16}$ hydrocarboon containing seven rings and a C/H atomic ratio of 0.876.

The primary alcohol is a reactant but it also can serve as a solvent. As a solvent it reduces the viscosity of the Binor-S while it is undergoing alcoholysis,. As a reactant it is the source of the R—CH₂—O— which contribute to the production of the ether. A primary alcohol is one which has a general structure R—CH₂OH wherein R is an alkyl or a hydrogen. As used herein "alkyl" refers to $C_nH_{2n}+1$ or a cycloalkyl referring to $C_nH_{2n}-1$. The number of carbon atoms in the alkyl may be as many as 20; however, it is preferred that the alkyl contains no more than 10 carbon atoms. A preferred alkyl is a paraffinic alkyl. The amount of alcohol present can vary to a trace whereby the amount of ether formed is also a trace amount to an amount in substantial excess of that necessary to react with all the Binor-S. An operative amount of alcohol would vary between about 1 to 1000 mole percent based on the moles of Binor-S; a more operative amount would be about 10 to 500.

Examples of the foregoing monohydric alcohols are methyl, ethyl, n-amyl, n-decyl, cetyl and stearyl. Examples of the foregoing monohydric cycloalkyl alcohols are cyclopropylcarbinol ($C_4H_8O$) and cyclohexylcarbinol.

The hydrogen used is free of sulfur or sulfur containing compounds. Any other impurity in the hydrogen which adversely effects the reaction, catalyst or products cannot be present.

The method of alcoholysis of Binor-S includes the presence of a promoter containing halide. The promoter can be a hydrogen-halide itself, e.g., hydrogen bromide or it can be from an aorganic halide such as ethyl chloride, isopropyl iodide, n-amyl bromide, ethylidene bromide, fluorobenzene, p-chlorotoluene, cyclopentyl chloride and the like. Alkyl halides, such as cyclohexylbromide are preferred. An alkyl halide is favored because an alkylhalide is more easily handled than the corresponding hydrogen halide. Of the four halides, i.e., fluoride, chloride, bromide and iodide, bromide is preferred. When an alkylhalide is used cyclohexylbromide, t-butyl chloride, isopropyl bromide and isopropyl chloride are preferred. In the presence of hydrogen and Raney nickel, palladium-on-carbon catalyst (hereinafter Pd/C), or palladium-on-alumina (hereinafter Pd/a) cause the alkylhalide to form the corresponding saturated alkyl hydrocarbon and the halide acid.

The amount of promoter containing halide present should be a promoting amount. While higher amounts accelerate reaction rates, too much could be uneconomical. An operative range is about 0.0001 to 0.004 gram moles of equivalent hydrogen halide per gram of Binor-S, a preferred range is about 0.0002 to 0.002. Equivalent hydrogen halide means either the amount of hydrogen halide used or that formed by the complete liberation of hydrogen halide from the organic halide.

The alcoholysis catalyst can be Raney nickel, Pd/C, or Pd/a. Normally the Pd/C contains about 0.5–12 weight percent palladium with a higher percentage, e.g., 10% preferred. Generally the amount of the catalyst present is that amount which is effective to catalyze the reaction. Typical operative ranges include about 0.1–10.0 weight percent based on the amount of Binor-S to be treated; a more operative range is about 0.5–5.0 weight percent.

The ionic alcoholysis of the Binor-S can be represented by the following formula reaction:

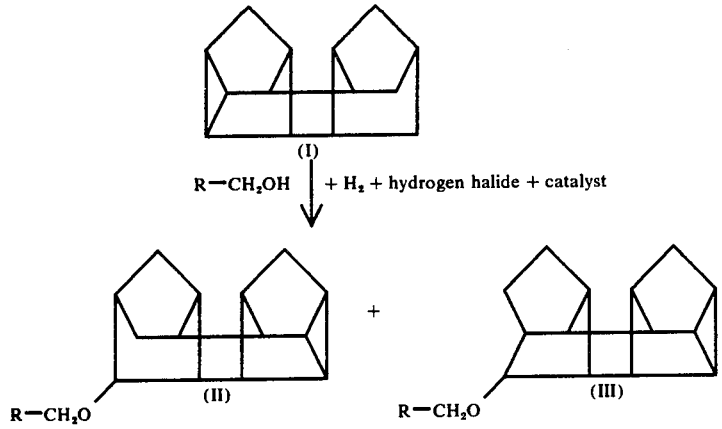

Compounds II and III accumulate with time and surprisingly further alcoholysis does not seem to occur. It appears that the monofunctional hexacyclic ether is resistant to further attack by a hydrogen halide.

The resulting mixture of present invention can contain unreacted I as well as ethers II and III. Other hydrocarbons can be present. The amount of ethers II and III present depend upon reaction times and the amount of alcohol present and other such variables. However, a mixture containing at least about 30 weight % of the ethers can be used as a sensitizer, mixture containing at least about 40% is preferred while one containing at least about 50% is more preferred.

Influencing the melting point of applicants' resulting mixture is the amount of unreacted high melting Binor-S contained therein. As the required melting point decreases the amount of unreacted Binor-S that can be present decreases. Unwanted and unreacted Binor-S can be removed by fractional crystallization, for example, or other known techniques. Also the amount of unreacted Binor-S remaining can depend on whether or not the fuel is heated to avoid fluid flow problems caused by ambient freezing temperatures.

The resulting mixture prepared by ionic alcoholysis of Binor-S has physical properties such as viscosity, density and heating value which enable it to be used as a sensitizer. For example, the entire product of one alcoholysis run has a pour point of $-75°$ F. ($-59.3°$ C), a density of 1.0987 and a net volumetric heat of combustion of 159,600 BTU gallon.

To practice the invention, for example, a suitable amount of the sensitizer containing the ether is incorporated into an inorganic nitrate or mixture thereof. The amount of the sensitizer is such that an oxygen balance of about $\pm 15\%$ is obtained. One way of defining a 100% oxygen balance is that all of the oxygen in the nitrate including ether is converted to an oxide. Another way of defining an oxygen balance is that all of the oxygen is stoichiometrically used if the reaction is 100% complete. Thus if the reaction is 100% complete all the carbon in the sensitizer is converted to $CO_2$, and all the hydrogen in the sensitizer is converted to $H_2O$, and all of the hydrogen in ammonium nitrate is converted to $H_2O$ while the nitrogen in the nitrate is released as nitrogen. Nevertheless, while a 100% oxygen balance is a desirable theoretical amount, practical considerations permit the use of a mixture which has either a reasonable excess or deficiency of oxygen. Generally the oxygen balance can be within $\pm 15\%$ while $\pm 10\%$ is a preferred value with $\pm 7.5\%$ more preferred.

EXAMPLES

Preparation of Ethers 10.6 grams of Binor-S was contacted with 100 milliliters of methanol, 0.4 grams of Raney nickel. The Binor-S, because of its preparation from norbornadiene (bicyclo[2.2.1]hepta-2,5-diene) via dimerization with the catalyst system $CoBr_2$-(triphenyl-phosphine)$_2$-boron trifluoride etherate already contained an indigenous hydrogen halide. The contacting was conducted at temperatures within 150°–230° C. and at pressures within 200–2700 psig in a high pressure, rocking type reaction of 0.3 liter capacity. During the methanolysis, periodic monitoring of the contents of the reaction was carried out by withdrawing small samples from the liquid phase through a vent tube in the reactor. The samples were analyzed by high-efficiency capillary vapor phase chromatography with electronic integration of the data.

Results of methanolysis of the Binor-S are shown in the accompanying table. After 40 hours the product mixture contained 48.7% of alkyl ethers of Binor-S. However, 3.75 hours later the amount of ether decreased. It is believed that this decrease does not reflect a change in composition but rather reflects the reproducibility of the particular instrument used for analysis.

Reflecting this question of reproducibility is the fact that the same product, i.e., the one after 43.75 hours, was analyzed on another vapor phase chromatography instrument. The results on this instrument are as follows: 13% Binor-S, 5% pentacyclics, 47% hexacyclics and 34% ether. The entire product had a pour point of −75° F., a density of 1.0987 and a net volumetric heat of combustion of 159,600 BTU/gallon.

Infrared, mass and NMR (nuclear magnetic resonance) studies confirmed that the ether is a methoxy substituted hexacyclic material with an intact cyclopropane ring and with the ether group attached to a secondary carbon rather than to a bridgehead position.

Analogous results will be obtained when the alcohol is ethyl, propyl, n-butyl, isobutyl, n-amyl, n-decyl, cetyl and stearyl. Equally analogous results will be obtained when cyclopropylcarbinol or cyclohexylcarbinol is used. Also equivalent results will be obtained when Pd/C or Pd/a is used.

TABLE

| METHANOLYSIS OF BINOR-S WITH RANEY NICKEL | | |
|---|---|---|
| Reaction Time, hrs. | 40 | 43.75 |
| Temperature, ° C | 200 | 230 |
| Pressure, psig | 2000 | 2700 |
| Product, %+ | | |
| Binor-S | 16.7 | 15.8 |
| Ethers of Binor-S | 48.7 | 43.3 |
| Hexacyclics | 30.0 | 36.7 |
| Unknowns | 5.2 | 4.2 |
| TOTAL | 100.6 | 100.0 |

+% are areas based on curves from vapor phase chromatography.

USE OF MIXTURE

A hole is drilled in the earth with a mechanical drill. The latter can be a rotary drill using a very hard material such as diamonds. Other types of drills such as jet-piercing drills can be used. The depth of the hole can range from a few feet to several hundred feet or more. The diameter of the hole can vary from about 1 to about 12 inches.

After the hole is drilled the desired amount of inorganic nitrate, for example, ammonium nitrate, is poured into the hole. Then the desired amount of the sensitizer containing the alkyl ether of Binor-S is poured into the hole containing the nitrate. In this example, the desired amount is that sufficient to obtain about a 100% oxygen balance. The amount is determined by a calculation based on the reaction equation.

After the nitrate and the ether containing mixture is placed in the hole, a blasting cap is added. The hole is confined and then the cap is detonated which in turn sets off the nitrate-ether mixture. The resulting blast is commercially attractive in that a smaller amount of explosive obtained a blast equal to a larger amount of AN-DF Mixture.

Other mixtures of nitrates, such as one containing ammonium nitrate and sodium nitrate, give analogous results. Also use of other sensitizers containing different amounts of the ether or ethers prepared using alcohols other than methanol will give analogous results.

The invention claimed is:

1. An improved method of blasting wherein a hole is drilled and then filled with both an inorganic nitrate or mixture thereof and a liquid sensitizer and then a detonator is placed in the hole, and then the nitrate, the hydrocarbon and the detonator are confined and then the detonator is activated thereby causing a blast; the improvement comprises that the sensitizer contains at least about 30% by weight of alkyl ether of Binor-S and wherein the amount of sensitizer is within ±15% of an oxygen balance.

2. An improved method according to claim 1 wherein the inorganic nitrate is selected from the group consisting of ammonium nitrate, mixture of a major amount of ammonium nitrate and a minor amount of sodium nitrate, potassium nitrate, calcium nitrate, magnesium nitrate and a mixture of the minor nitrates.

3. An improved method according to claim 1 wherein the amount of the ether is within ±10% of an oxygen balance.

4. A blasting composition comprising a mixture of both a. an inorganic nitrate selected from the group consisting of ammonium nitrate, mixture of a major amount of ammonium nitrate and a minor amount of sodium nitrate, potassium nitrate, calcium nitrate, magnesium nitrate and a mixture of the minor nitrates; and b. a sensitizer containing at about 30% by weight of alkyl ether of Binor-S; and wherein the amount of the sensitizer is within ±15% of an oxygen balance.

5. A composition according to claim 4 wherein the amount of the sensitizer is within ±10% of an oxygen balance.

* * * * *